United States Patent
Vergeer

(10) Patent No.: US 9,484,188 B2
(45) Date of Patent: Nov. 1, 2016

(54) INDIVIDUAL BEAM PATTERN PLACEMENT VERIFICATION IN MULTIPLE BEAM LITHOGRAPHY

(71) Applicant: MAPPER LITHOGRAPHY IP B.V., Delft (NL)

(72) Inventor: Niels Vergeer, Rotterdam (NL)

(73) Assignee: MAPPER LITHOGRAPHY IP B.V., Delft (NL)

(*) Notice: Subject to any disclaimer, the term of this patent is extended or adjusted under 35 U.S.C. 154(b) by 0 days.

(21) Appl. No.: 14/644,261

(22) Filed: Mar. 11, 2015

(65) Prior Publication Data

US 2016/0268099 A1 Sep. 15, 2016

(51) Int. Cl.
| | |
|---|---|
| G03F 1/00 | (2012.01) |
| G03F 9/00 | (2006.01) |
| H01J 37/317 | (2006.01) |
| G01N 21/88 | (2006.01) |

(52) U.S. Cl.
CPC ........... *H01J 37/3177* (2013.01); *G01N 21/88* (2013.01)

(58) Field of Classification Search
CPC ...... G03F 9/7049; G03F 9/00; G03F 9/7011; G03F 9/7026; G03F 9/7034; G03F 9/7076; G03F 9/7092; G03F 9/7096; H01J 37/3045; H01J 37/3177; H01J 37/3174
USPC .......... 250/398, 396 ML, 396 R, 397, 492.1, 250/492.2, 492.3, 548; 355/72; 356/400, 356/237.2, 401, 509, 512
See application file for complete search history.

(56) References Cited

U.S. PATENT DOCUMENTS

| | | | |
|---|---|---|---|
| 6,897,458 B2 | 5/2005 | Wieland et al. | |
| 6,946,665 B2 | 9/2005 | Muraki et al. | |
| 6,958,804 B2 | 10/2005 | Wieland et al. | |
| 6,992,766 B2 * | 1/2006 | Tanaka ................ | G03F 9/7011 250/548 |
| 7,019,908 B2 | 3/2006 | vant Spijker et al. | |
| 7,084,414 B2 | 8/2006 | Wieland et al. | |
| 7,129,502 B2 | 10/2006 | Kruit | |

(Continued)

FOREIGN PATENT DOCUMENTS

| | | |
|---|---|---|
| EP | 1434103 A2 | 6/2004 |
| EP | 2 131 243 A2 | 12/2009 |

(Continued)

OTHER PUBLICATIONS

Dr. Lynn Fuller, "Wafer Alignment for Canon Stepper", Rochester Institute of Technology, Microelectronic Engineering, Jan. 14, 2008, p. 1-74.

*Primary Examiner* — David A Vanore
(74) *Attorney, Agent, or Firm* — Hoyng Rock Monegier LLP; David P. Owen

(57) ABSTRACT

Methods and systems for verification of a mark written on a target surface during a multiple beam lithography process, and for verifying beam position of individual beams on the target surface based on mark verification are disclosed. A mark can be verified by scanning an optical beam over the mark and measuring the reflected optical beam and the position of the target with respect to the optical beam. By comparing the intensity of the reflected light as a function of distance over the mark with reference mark data representing an intended definition of the mark, and any deviation between the measured representation and the reference mark data are determined. If any deviation deviate more than the predetermined limit, incorrectly positioned beams can be verified from the data.

25 Claims, 9 Drawing Sheets

(56) References Cited

U.S. PATENT DOCUMENTS

| | | | |
|---|---|---|---|
| 7,298,496 B2 * | 11/2007 | Hill | G01B 11/2441 356/237.2 |
| 7,418,125 B2 * | 8/2008 | Miyashita | G06K 9/3233 382/151 |
| 7,466,414 B2 | 12/2008 | Tanaka et al. | |
| 7,709,815 B2 | 5/2010 | Jager et al. | |
| 7,842,936 B2 | 11/2010 | Kruit et al. | |
| 7,868,300 B2 * | 1/2011 | Kruit | B82Y 10/00 250/396 ML |
| 8,089,056 B2 | 1/2012 | Wieland et al. | |
| 8,254,484 B2 | 8/2012 | Kim et al. | |
| 8,582,114 B2 * | 11/2013 | Manassen | G03F 7/70633 356/509 |
| 9,201,315 B2 * | 12/2015 | De Boer | G03F 9/7088 |
| 2003/0046821 A1 * | 3/2003 | Horie | G03F 7/70616 33/297 |
| 2003/0215965 A1 * | 11/2003 | Grodnensky | G03F 7/70625 438/16 |
| 2004/0066518 A1 | 4/2004 | Kreuzer | |
| 2006/0061743 A1 | 3/2006 | den Boef et al. | |
| 2007/0064213 A1 | 3/2007 | Jager et al. | |
| 2007/0153275 A1 | 7/2007 | Aa et al. | |
| 2008/0013090 A1 * | 1/2008 | Hagiwara | G03F 9/7026 356/400 |
| 2009/0053629 A1 * | 2/2009 | Shibazaki | G03F 7/70775 430/30 |
| 2009/0176167 A1 | 7/2009 | Hulsebos et al. | |
| 2009/0237637 A1 | 9/2009 | Warnaar et al. | |
| 2009/0261267 A1 | 10/2009 | Wieland et al. | |
| 2011/0073782 A1 | 3/2011 | Wieland | |
| 2012/0091358 A1 | 4/2012 | Wieland et al. | |
| 2012/0133938 A1 | 5/2012 | Deckers et al. | |
| 2012/0267802 A1 * | 10/2012 | De Boer | G03F 9/7088 257/797 |
| 2012/0268724 A1 | 10/2012 | de Boer et al. | |
| 2012/0268725 A1 | 10/2012 | de Boer et al. | |
| 2012/0293810 A1 | 11/2012 | Meijer | |
| 2014/0322833 A1 * | 10/2014 | Yamaguchi | H01J 37/3045 438/14 |
| 2015/0109598 A1 * | 4/2015 | Vergeer | G03F 9/7088 355/72 |

FOREIGN PATENT DOCUMENTS

| | | |
|---|---|---|
| WO | WO 2007 038134 A2 | 4/2007 |
| WO | WO 2013029893 A2 | 3/2013 |
| WO | WO 2014 064290 A1 | 5/2014 |

* cited by examiner

*Fig. 2*
*(Prior Art)*
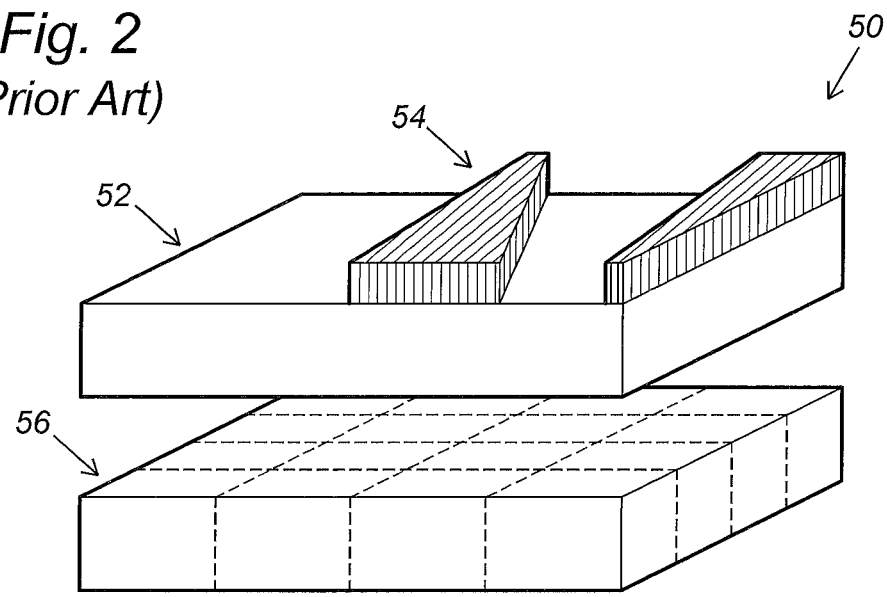
*Fig. 2A*
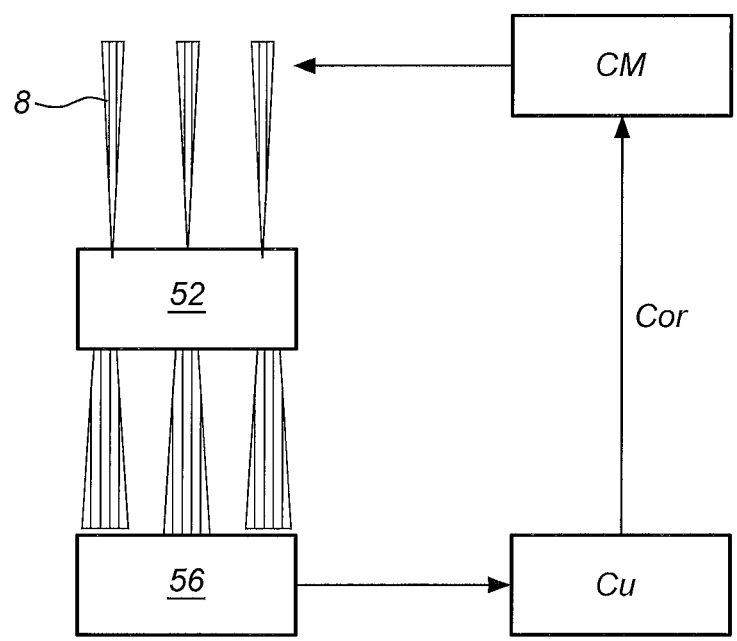
*Fig. 2B*

INDIVIDUAL BEAM PATTERN PLACEMENT VERIFICATION IN MULTIPLE BEAM LITHOGRAPHY

TECHNICAL FIELD

The disclosure relates to methods and systems for verification, including verification of marks written by multiple beam lithography, individual beam pattern placement and individual beam positions on a target surface in a multiple beam lithography apparatus.

BACKGROUND

In multiple beam lithography, such as charged particle beam lithography, small structures may be formed, i.e. written, with high accuracy and reliability. In charged particle lithography charged particles are directed onto a target surface, typically a wafer surface, to form patterns which may form the basis for integrated circuits and components thereof. In multiple beam lithography the pattern formed on the surface is determined by the position where each individual beam interacts with the resist on the surface.

Lithographic processing generally involves multiple exposures of layers, so that features formed in subsequent layers may be connected to create an integrated circuit. Therefore, not only each pattern itself has to meet the required accuracy, but it is also a requirement that a pattern exposed in a later exposure session is aligned with the one or more patterns created in earlier exposure sessions in a sufficiently accurate manner.

While in optical lithography the pattern is formed by illumination of a target surface through a mask, the accuracy and quality of the resulting pattern influenced by the accuracy of the mask, in multiple beam lithography the pattern is determined by the position where each individual beam interacts with the surface. In multiple beam lithography it is therefore of importance that each individual beam is correctly positioned, such that it impinges at the intended position on the surface in order that the intended pattern is formed. This is often referred to as pattern placement accuracy.

Various technologies for measuring beam properties and pattern placement properties have been developed.

US 2012/0268724 A1 describes methods and systems for aligning the target with the optical column of a multiple beam lithography apparatus. Further, determination of a spatial distribution of beam properties are described, using a beam measurement sensor positioned on the chuck.

U.S. Pat. No. 7,868,300 B2 and US 2012/0293810 A1 describe methods and systems for measuring beam properties using a sensor having a surface comprising beam blocking and non-blocking regions, also known as knife edge measurements. The sensor surface may be positioned at a position corresponding to the position of the target surface during lithography.

Although methods and systems described in the documents cited above enable measurement of beam properties, such as spatial distribution of beams, these do not enable verification of the pattern placement accuracy.

A known method for verifying the result of a lithography process is offered by scanning electron microscopy (SEM), such as critical dimension SEM (CD-SEM). In CD-SEM the CD-uniformity can be verified by measuring dimensions of features formed on the surface. While SEM offers high enough resolution for studying dimensions of interest in semiconductor technology, the field of view is limited to surface areas with dimensions of a few $\mu m^2$. Therefore, it is not possible to observe a pattern having contributions from each individual beam used during the multiple beam lithography. In order to verify pattern placement accuracy for all beams, the measurement procedure has to be repeated for several measurement areas. The CD-SEM method is therefore time consuming.

SUMMARY

In multiple beam lithography, it would be advantageous to be able to verify the position of each individual beam on the target surface. It is an object of the present disclosure to provide a method and a system for verifying the position of each individual beam on a target surface in a multiple beam lithography apparatus. It is further an object to provide a method and a system for verifying marks formed, in particular written, by multiple beam lithography. A further object is to sort wafers or portions of wafers based on the verification of such marks.

According to the present disclosure, verification of beam positions in a multiple beam lithography apparatus, i.e., individual pattern placement accuracy determination, is performed by verifying a mark written on the target surface by the lithography apparatus. An incorrect position of one or more beams will cause corresponding portions of the mark to deviate from specifications of the mark. Determining the presence and location of such deviation or deviations enables identification of incorrectly positioned beams. The measurements may be performed within the lithography apparatus. Thereby individual beam pattern placement accuracy may be determined with high accuracy within a short amount of time. The solution presented herein therefore offers a considerable time saving compared to SEM measurements.

A method for verification of a mark written or formed on a target surface during a multiple beam lithography process is disclosed. The method comprises the following steps:
mark measurement, comprising:
  directing, and preferably focusing, an optical beam onto the target surface;
  measuring a reflected optical beam generated by reflection of the optical beam by the surface;
  moving the optical beam and the target with respect to one another such that the optical beam is scanned over at least one scan line across at least a portion of the mark in a direction parallel to a first axis;
  measuring an intensity of the reflected optical beam as a function of position along the scan line; and
  obtaining a measured representation of the mark, the measured representation comprising intensity as a function of position along the scan line and/or parameters calculated from said intensity;
comparing the measured representation with reference data representing an intended definition of the mark and determining any deviation or deviations between the measured representation and the reference data.

The mark, or pattern, comprises features having dimensions which may be resolved by the optical beam reflection measurement. It may comprise a pattern or pattern portion designated for this purpose. In particular, the mark may comprise features each written, or formed, by one individual beam.

The method allows for verification of a mark, within a short time. Typically, an optical scan line over the mark may take a few seconds, on the order of 1-10 seconds.

The first axis may be an axis perpendicular to stripe areas on the target surface. A stripe is an area intended for writing by one single beam during a multiple beam lithography process, aligned with the long stroke direction in a multiple beam lithography apparatus, the long stroke direction being the direction along which the target is scanned during patterning of the target.

The optical beam is reflected by areas having different reflectivity, appearing in the resist layer after development depending on whether or not the resist layer areas have been exposed during the lithography process, and/or areas having topography variations, e.g. resulting after etching of the target surface, giving rise to intensity variation in the reflected optical beam. Differences in reflection coefficient and/or topography typically results from one or more semiconductor processing steps of the exposed target surface. A pattern may be visible in the resist layer after development of the resist layer. Alternatively, measurements may be performed after etching of the semiconductor surface, the etching being subsequent to development and partial removal of the resist layer, giving rise to height variations on the target surface. Alternatively, the measurement may be performed after deposition of one or more layers on the target surface, subsequent to resist development, and possibly etching of the surface. The surface treatment after which mark measurement is performed may be a matter of choice depending on, for example, properties of the resist used, and/or the kind of processing steps intended for the specific target. Thereby, verification of a mark and pattern placement verification can be performed at various stages of the semiconductor processing of the target surface. The target surface may be moved relative the optical beam using a target actuator, and the relative position, or at least a change in the relative position, may be measured, for example by an interferometer arrangement, or be deducted from actuator control and/or feedback data.

The measured representation may comprise distances between adjacent maxima or minima in a graph of intensity versus position on the mark. Parameters calculated from the intensity may comprise distances between, or dimensions of, different features of the mark. If all detected deviations between data obtained from the measurements and reference data, i.e. the specification of the mark, are smaller than a limit value, the mark may be considered to comply with its specification and may be verified. If there is at least one deviation which exceeds the limit, the mark is considered not to comply with the reference, and may be considered not verified.

If one or more of the deviations is not within a predetermined limit, error position data may be determined, specifying positions where the measured representation deviates from the reference data by more than the predetermined limit. Coordinates specifying error positions in two dimensions may be determined. From the error position data, incorrectly positioned beams in the multiple beam lithography apparatus having written the mark may be identified.

The optical beam preferably comprises monochromatic light in the visible light range. It may comprise laser light, preferably having a wavelength in the range of 600-650 nm, preferably 630-635 nm. The laser light may be coherent or incoherent. An advantage with incoherent light may be less sensitivity to vibrations or other noise in the system. The wavelength may be chosen to enable high resolution while at the same time limiting influence on the resist layer caused by the optical beam. The optical beam is preferably focused onto the surface, typically to a spot having a diameter of about 1 or 600 nm, or any value there between. Preferably, the optical beam is directed toward the surface at an angle of substantially 90° with respect to a plane defining the target surface. Preferably, a $0^{th}$ order reflection of the optical beam from the surface is measured.

The optical beam may be scanned over a plurality of substantially parallel scan lines. The distance between adjacent scan lines may be of the same order of magnitude as a stripe width. The measured representation may be obtained by calculating distances between adjacent features comprised within the mark, calculating the distance between all of the features within the scan lines, and calculating the distances for each scan line. By performing a plurality of scan lines different areas or portions of the mark may be measured. Thereby mark verification may be performed with higher accuracy. The distance between scan lines may be determined by measurement of the relative position and/or movement of the target with respect to the optical system.

The method may comprise forming a mark on said target surface using a multiple beam lithography apparatus and determining individual beam pattern placement accuracy based verification of the mark, and determining that one or more of the beams within the multiple beam lithography apparatus are incorrectly positioned if one or more of the deviations is not within the predetermined limit. The step of forming a mark comprises lithographic patterning, by means of writing a pattern on the target surface, and subsequent surface treatment of the target surface. Such surface treatment comprises steps known in semiconductor fabrication, e.g. one or more steps of resist development, etching, deposition of one or more materials, material implantation, etc. If any deviations are all within the predetermined limit, the beams are determined to be correctly positioned on the target surface. The measurement may be performed within the lithography chamber, after semiconductor processing of the patterned target surface. Semiconductor processing of the target surface may be any one or more of steps such as resist development, partial removal of resist layer, etching of the exposed semiconductor surface, deposition of one or more materials on the exposed, and eventually etched, semiconductor surface, etc, known in semiconductor industry. The mark measurement is thus performed after processing of the target outside of vacuum. Mark measurement may be performed prior to a following lithographic exposure session of the target surface. Alternatively or analogously, patterning, surface treatment, and measurement may be performed as an initial calibration or lithography tool verification process, prior to the intended patterning.

Incorrectly positioned beams may be identified using the error position data. Since each feature within the mark may be associated with an individual beam having written this feature, any error detected in the mark may be associated with a specific individual beam. Since preferably all beams are represented in the mark any incorrectly positioned beams can be identified.

The mark, also referred to as test mark, preferably enables verification of individual beam positions in two dimensions on the target surface for each beam used for writing the mark, for each beam used in the lithography apparatus. The mark preferably comprises at least one feature written by each individual beam, enabling verification of beam position along the first axis, the features further enabling, or additional features written by each individual beam enabling, verification of beam positions along a second axis, substantially perpendicular to the first axis. The mark thus comprises individual features written by each individual beam.

The one or more scan lines may extend over a plurality, preferably all, features comprised in the mark. By scanning the optical beam over all lines comprised in the mark, the position of each beam used for writing the test mark may be verified.

The mark may comprise a number of lines each written by one beam during the multiple beam lithography. The number of lines preferably corresponds to at least the number of beams used during the lithography. The mark may comprise:
- a first portion wherein the lines form straight parallel line portions oriented at an oblique angle α with respect to the first axis,
- a second portion wherein the lines form straight parallel line portions oriented perpendicular to the first axis, and
- a third portion wherein the lines form straight parallel line portions oriented at an oblique angle α+90° with respect to the first axis. The angle α preferably has a value of substantially 45°. The portions defined above may alternatively be arranged in a different order.

Preferably, each beam used during the multiple beam lithography is represented in the first, second and third portions of the test mark. The extension of the different portions along a second axis, perpendicular to the first axis, are preferably of the same order of magnitude as the stripe width, which is typically about 2 μm. The extension of the mark along the second axis may be, at least, around 5 to 10 μm. By forming the mark with a certain extension along the second axis and performing scans at different positions along the second axis, effects due to wafer processing, such as step height variation, CDu, etc., can be averaged out.

The lines may have a dimension in the first direction comparable to the size of the optical beam spot. For example, the lines may be 1 μm wide, which typically corresponds to half the stripe width. The lines may be positioned substantially in the center of each stripe. The lines may thus be patterned by the individual beams being deflected, to a limited amount, around their central position during patterning.

A first scan line may be performed within the first portion, a second scan line within the second portion, and a third scan line within the third portion. Alternatively, the scan lines may be performed in a different order. A position of a beam along the first axis may be determined from the intensity measured along the second scan line, over line portions oriented along the second axis. By combining the intensity values measured along the second scan line and the first and/or third scan line a position of the beam along the first axis and the second axis are determined. Measurement data from a scan line over the second portion in combination with a scan line over one of the first or third portions may be sufficient to deduct beam position along the second axis. In principle, it would therefore be sufficient for the mark to comprise those regions. However, using an additional region, with the diagonal lines oriented in the opposite direction, provides redundancy and may provide more accurate pattern placement measurement. Preferably, the positions are verified for each beam used for forming the test mark.

The line portions oriented at an angle α with respect to the first axis, also referred to as diagonal lines, may be used for verification of beam position along the second axis. A position error of a beam along the second axis of a beam direction will lead to a shift −d in one diagonal line and a shift of +d in the oppositely oriented diagonal line. Thereby, by writing two diagonal line parts, oriented substantially perpendicular to one another, a position error along the second axis of a beam may be deducted from optical scans over these line parts. From the straight line portion, i.e. the line portion oriented perpendicular to the first axis, beam position along the first axis may be deducted. Thereby, two-dimensional pattern placement verification may be performed.

The mark measurement may be performed within a multiple beam lithography apparatus. Verification of beam positions on the target surface may thus be performed within the lithography apparatus. The measurements may be performed using a sensor which may already be present in the lithography chamber. In particular, a sensor for measuring alignment marks may be used. The target may be positioned on a target support, and the target support actuators present in the lithography apparatus may be used for moving the target with respect to the optical beam such as to perform one or more scan lines over the mark.

Features in the mark may be related to individual beams by determining a position of the target with respect to a lithography apparatus reference point. A central axis of the lithography optical column, and especially its point of coincidence with the target surface, may define the lithography apparatus reference point. A relative position of the target with respect to the target support may be determined, and a relative position between the target support and the lithography apparatus reference point may be determined. A relative position between the target and the lithography apparatus reference point may thereby be determined. One or more of these relative distances may be taken into account for relating features of the mark to one or more beams.

Since beam positions on the target surface provides the largest contribution to stitching properties, i.e. pattern correctness in boundary regions between adjacent stripes, verification of beam positions as described herein provides for verification of stitching properties. The method may comprise verifying overlay. In order to enable overlay verification, the mark comprises a first set of features formed in a first layer and a second set of features formed in a second layer, whereby the second layer is formed on top of the first layer. The different sets of features may be formed in subsequent exposure sessions. Overlay can be verified by measuring the relative position of features in the first set with respect to features in the second set of features, and comparing the measured relative positions with reference data specifying the intended relative position. As above, distances between features may be measured.

The method may comprise performing calibration and/or compensation of incorrectly positioned beams. Parameters of one or more electron optical components controlling the incorrectly positioned beam may be modified, for example to recalibrate beam position, and/or blanking incorrectly positioned beams. Compensation may be realized by changing the pattern specification data, such that one or more correctly positioned beams are used to write the features which should have been written by the incorrectly positioned beam.

The mark verification method may be used for sorting wafers, or portions thereof, comprising one or more marks written in a multiple beam lithography process, based on verification of the mark. One or more test marks may be positioned in one or more areas on the wafer surface which are not used for formation of dies and/or microelectronic circuits. For example, marks may be formed in regions comprising an area first scanned and a final area scanned during a lithography process, respectively. The mark may extend over an area associated with a row of die areas on the wafer. The mark may be formed along the full width of the wafer. The portions of the wafer may be sorted, marked or otherwise indicated for further processing or rejection based on whether or not any deviations within associated marks are within said predetermined limit. Further processing of the wafer may comprise any fabrication step present during semiconductor wafer processing. Individual die areas may thus be sorted based on whether associated test marks comply with test mark specifications. If a test mark formed on the target surface does not correspond to reference data, this may indicate that other patterns formed on the wafer during the lithography process also do not comply with specifications. Further testing, such as electronic testing of dies, may be obsolete.

Mark measurement may be performed in a separate chamber, arranged separated from, e.g. downstream, the lithography apparatus. By using a separate chamber the measurement may be performed without influencing the throughput of the lithography apparatus. All wafers processed in the lithography system may be subjected to measurement, or samples out of a batch may be measured.

Alternative to the above, a mark as described above written on the target surface, in particular a mark having contributions from individual beams, may be verified by photographic and image processing methods. For this alternative process, a camera enabling very high resolution is required. The distances between individual features may be deducted from a highly magnified photo and compared to reference data as described above. This may be performed by image analysis. However, such methods puts high requirements on the camera, e.g. in terms of resolution and accuracy. Furthermore, this technique is sensitive to noise.

The herein described method of measuring the reflection of a light beam scanned over the mark offers a higher signal to noise ratio, and thereby a more accurate measurement. Furthermore, it can be performed using sensors already present in the lithography chamber, which offers a less complex system.

A system for mark verification, in particular for individual beam pattern placement accuracy determination and/or wafer sorting, is described below. This system is preferably configured to perform one or more of the methods described above. The advantages and alternatives described above therefore analogously applies to the system.

A system for verification of a mark written on a target surface by a multiple beam lithography process is disclosed. The system comprises:
 a mark measurement unit, comprising:
  an optical system for directing, and preferably focusing, an optical beam onto the target surface and receiving a reflected optical beam generated by a reflection of the optical beam by the surface, and for generating an intensity signal representing an intensity of the reflected optical beam;
  a target support for supporting the target; and
  an actuator for moving the optical system and the target support with respect to one another along at least a first axis, such that the optical beam is scanned along at least one scan line over at least a portion of the mark;
  a control unit configured to:
   receive the intensity signal,
   receive a position signal representing a position of the target with respect to the optical system,
   register the intensity signal as a function of the position signal,
   obtain a measured representation of the mark, the measured representation comprising the intensity as a function of position and/or parameters calculated from the intensity values,
   compare the measured representation with reference mark data representing an intended definition of the pattern and determining any deviation or deviations between the measured representation and the reference mark data.

The optical system may be an optical system as described in US 2012/0268724 A1 and discussed with below relation to FIG. 4.

The control unit may be configured to determine error position data specifying positions where the measured representation deviates from the reference data by more than a predetermined limit. The control unit may be configured to obtain the measured representation by calculating distances between adjacent features comprised within the mark, as discussed above.

The mark measurement unit may be arranged in a vacuum chamber, such as a lithography chamber to enable verification of a mark created by the lithography apparatus. The optical system may be connected to a light source positioned outside the vacuum chamber. The control unit is preferably also positioned outside vacuum.

The actuator may be adapted to enable relative movement of the optical system and the target support also along a second axis, substantially perpendicular to the first axis. Thereby the optical beam may be scanned over a plurality of scan lines. The actuator may be configured to actuate movement along the second axis with an accuracy such that the distance between adjacent scan lines is on the same order of magnitude as a stripe.

The mark verification system may comprise a plurality of optical systems, preferably arranged in a row, substantially perpendicular to the first axis. Alternatively, the optical system may be configured to direct a plurality of optical beams onto the surface and measure the reflection of each optical beam.

The mark verification system may be configured for pattern placement accuracy determination. The control unit may be configured to verify positions of beams on the target surface during a lithography process based on verification of a mark formed, e.g. written, during the lithography process. Beam positions may be deemed to be correct if each of the deviations between the measured representation and the reference mark data is within the predetermined limit. The control unit may be configured to identify incorrectly positioned beams based on error position data if one or more of the deviations is not within the predetermined limit. The control unit may be configured to identify incorrectly positioned beams by correlating the error position data with one or more beams in the multiple beam lithography apparatus. By identifying which features of the mark are not complying with the reference data and correlating these features with the beams having written them, it can be determined which beams are not correctly positioned on the target surface.

The control unit may be configured to identify incorrectly positioned beams based on measurements on a mark allowing two dimensional pattern placement verification, as described above. The control unit may be configured to perform any calculations and/or data processing necessary to detect and identify any incorrectly positioned beams causing incorrect patterning of the surface.

The mark verification system may be configured for sorting wafers or portions of wafers provided with one or more test marks, in particular according to the method described above. The system may be configured to mark individual areas for further processing and/or rejection based on whether or not deviations in a region of a test mark associated there with is within the predetermined limit.

A multiple beam lithography apparatus, such as a multiple optical beam lithography apparatus or a multiple charged particle beam lithography apparatus, such as a multiple ion beam apparatus or a multiple electron beam apparatus, is disclosed. The multiple beam lithography apparatus comprises a lithography chamber, a lithography control unit, and a system for verifying individual beam positions as described above. The lithography chamber comprises a target support and a target support actuator adapted to move the target support along at least said first axis. The lithography system control unit is configured to control the multiple beam lithography apparatus, in particular to perform patterning of the target according to pattern specifications, and comprises or is configured to communicate with the mark verification control unit. The lithography control unit may be configured to control the lithography apparatus to form a mark on the surface, and to verify beam positions of the surface based on measurements on the mark. The mark may be a mark allowing verification of positions of individual beams on the target surface in two dimensions, as described above.

The mark measurement unit may be arranged within the lithography chamber, the actuator unit being the target support actuator. The target actuator is preferably adapted to move the target in two dimensions during a lithography process, which may correspond to the first and second axis, respectively. Thereby, measurements of marks written by the lithography apparatus may be performed, in particular it may be performed within the lithography chamber, and beam position verification may be performed subsequent to lithographic patterning, after semiconductor processing of the patterned target surface, as described above. The mark measurement unit may be located close to the optical column of the lithography apparatus, for example within a distance of 100 μm from an outer exposure beam used for patterning the target.

Alternatively or additionally, the mark measurement unit may be arranged in a separate chamber. Measurements and/or verifications of marks written during a lithography processes may thereby be performed independently from the lithographic process itself, such that lithographic patterning of targets may be performed without any eventual delay caused by mark verification measurements.

The lithography system may comprise an alignment sensor arrangement for determining and controlling a relative position of the target support and the lithography apparatus reference point, for example as described in US 2012/0268724 A1. The alignment sensor arrangement may comprise an alignment sensor for aligning the target with respect to the electron optical system. The alignment sensor may comprise the optical system of the mark measurement unit. The alignment sensor arrangement may also comprise the actuator and/or the mark verification control unit. According to the present disclosure, the alignment sensor may be used both for alignment of the target with respect to the optical column and for measuring marks written on the target surface by the lithography apparatus in order to perform individual beam pattern placement accuracy verification.

The lithography control unit may be configured to perform compensation and/or calibration of incorrectly positioned beams. As discussed above, the patterning strategy may be modified, such that incorrectly positioned beams are permanently blanked and the intended pattern written by the correctly positioned beams.

A computer program for verifying position of beams on a target in a multiple beam lithography apparatus, especially in a lithography system described above, is disclosed. The computer program is configured to:
control the lithography apparatus to write a mark on a target surface,
control an actuator to move the optical beam and the target with respect to one another such that the optical beam is scanned over at least a portion of the mark,
record the intensity as a function of position of the optical beam on the target,
determine a measured representation of the mark, the measured representation comprising intensity as a function of position and/or parameters calculated from the intensity,
compare the measured representation with reference mark data representing an intended definition of the mark,
determining any deviations between the measured representation and the reference mark data,
if one or more of the deviations is not within the predetermined limit, determine error position data specifying positions where the measured representation deviates from the reference mark data by more than the predetermined limit, and
identify incorrectly positioned beams based on the error position data.

The computer program may further be configured to control compensation of incorrectly positioned beams. The computer program may be configured to control a lithography system control unit to perform one or more of the methods described above. The computer program may be stored in the lithography control unit or in a medium in communication therewith.

BRIEF DESCRIPTION OF THE DRAWINGS

Various aspects of the disclosure will be further explained with reference to embodiments shown in the drawings wherein:
FIGS. 2A and 2B schematically show a beam measurement sensor according to prior art.

DESCRIPTION

Various embodiments of the methods and systems for mark measurement and beam position verification in multiple beam lithography according to the present disclosure are described below, given by way of example only and with reference to the figures.

Figure 1:
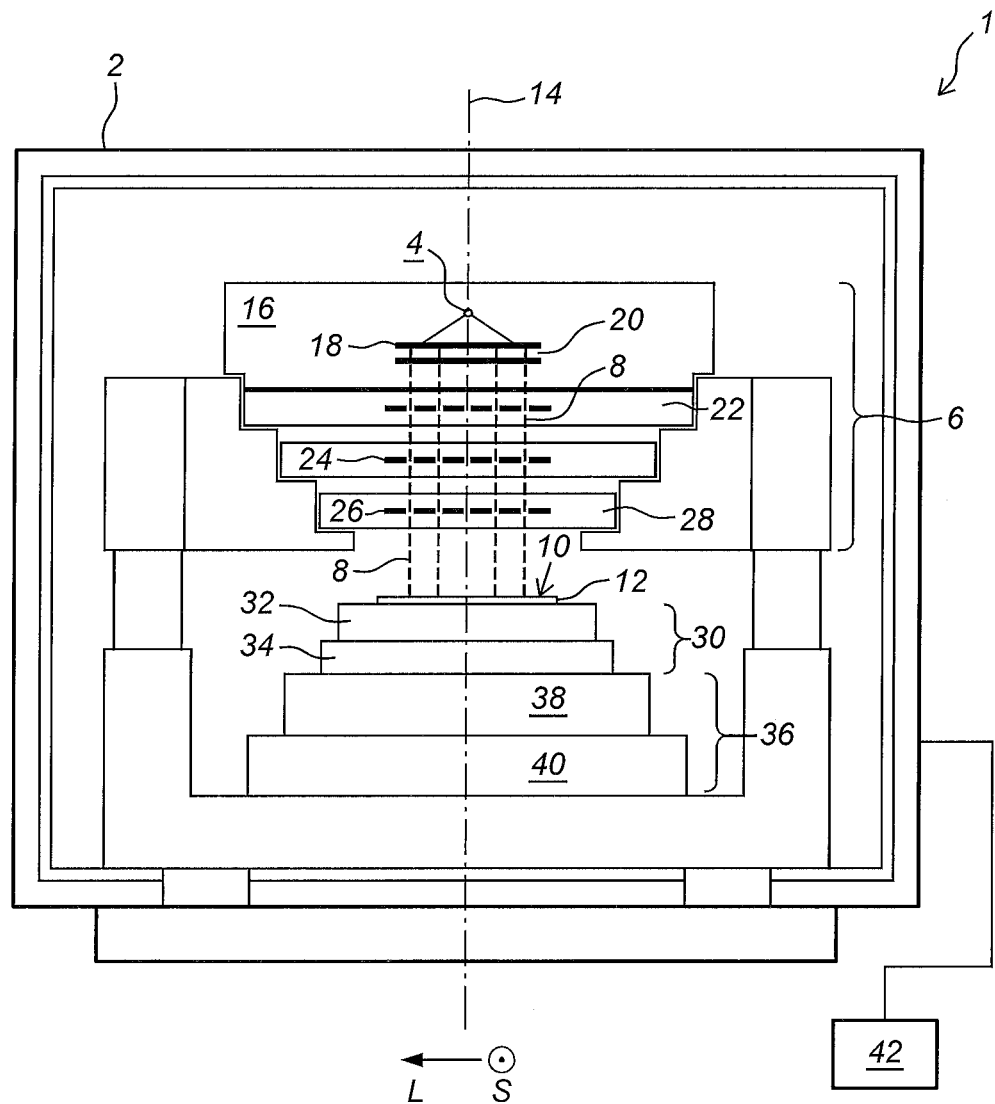
FIG. 1 schematically shows a multiple beam lithography system.

FIG. 1 shows a simplified schematic drawing of an embodiment of a charged particle multi-beam lithography system. Such lithography system is for example described in U.S. Pat. Nos. 6,897,458; 6,958,804; 7,019,908; 7,084,414; 7,129,502; 7,709,815; 7,842,936; 8,089,056 and 8,254,484; U.S. patent application publication nos. 2007/0064213; 2009/0261267; US 2011/0073782 and US 2012/0091358, assigned to the applicant of the present application and hereby incorporated by reference in their entirety. Although the lithography system is described below with reference to electron beams, the teaching applies to other types of individual beams as well.

The multi-beam lithography system 1 illustrated in FIG. 1 comprises a vacuum chamber 2, also referred to as lithography chamber, comprising an electron source 4 and an electron optical system 6 for forming and controlling beams 8 for patterning a surface 10 of a target 12, typically a silicon wafer coated with an electron sensitive resist layer. The components of the electron optical system 6 are aligned along an optical axis 14. An illumination optics module 16 comprising the electron source 4 and a beam collimating system 18 generates a collimated electron beam 20. In an aperture array and condenser lens module 22 the electron beam 20 is divided into a plurality of individual beams 8 which are directed to a beam blanker array 24. The blanker array 24 cooperates with a beam stop array 26 to blank beams 8 which are deflected by the blanker array, according to patterning data. Beams 8 which are not deflected by the blanker array 24 are transmitted through the beam stop array 26. The projection optics module 28, comprising the beam stop array 26, also comprises a deflector array (scanning deflector) and a focusing array (not illustrated). The deflector array deflects beams 8 in order to scan them over their respective writing areas, stripes, on the surface 10. The focusing lens array focuses the beams 8 onto the target surface 10.

The target 12 is supported by a target support 30, here a wafer table 32 mounted on a chuck 34. A target support actuator 36 is provided for moving the target support 30 with respect to the electron optical system 6, in particular with respect to the electron optical axis 14. The actuator 36 is preferably configured to provide movement of the target along a first axis and a second axis, in a plane substantially perpendicular to the optical axis 14. The actuator 36 may comprise a short stroke actuator 38 and a long stroke actuator 40.

A lithography control unit 42 is configured to control the lithography system, in particular the electron optical system 6 and the target support actuator 36 for patterning the target surface according to pattern specification data. The lithography control unit 42 may further be configured to control beam position verification based on mark verification, according to the verification methods described herein. Alternatively, the lithography control unit 42 may be configured to communicate with one or more separate control units controlling verification measurements. Further, the lithography control unit may be configured to perform and/or initialize compensation of incorrectly positioned beams and/or calibration of the electron optical system. The control unit 42 may comprise computer programs, or communicate with media comprising programs, controlling specified functions or methods when executed, such as target alignment measurements, target surface patterning, etc.

Figure 7:
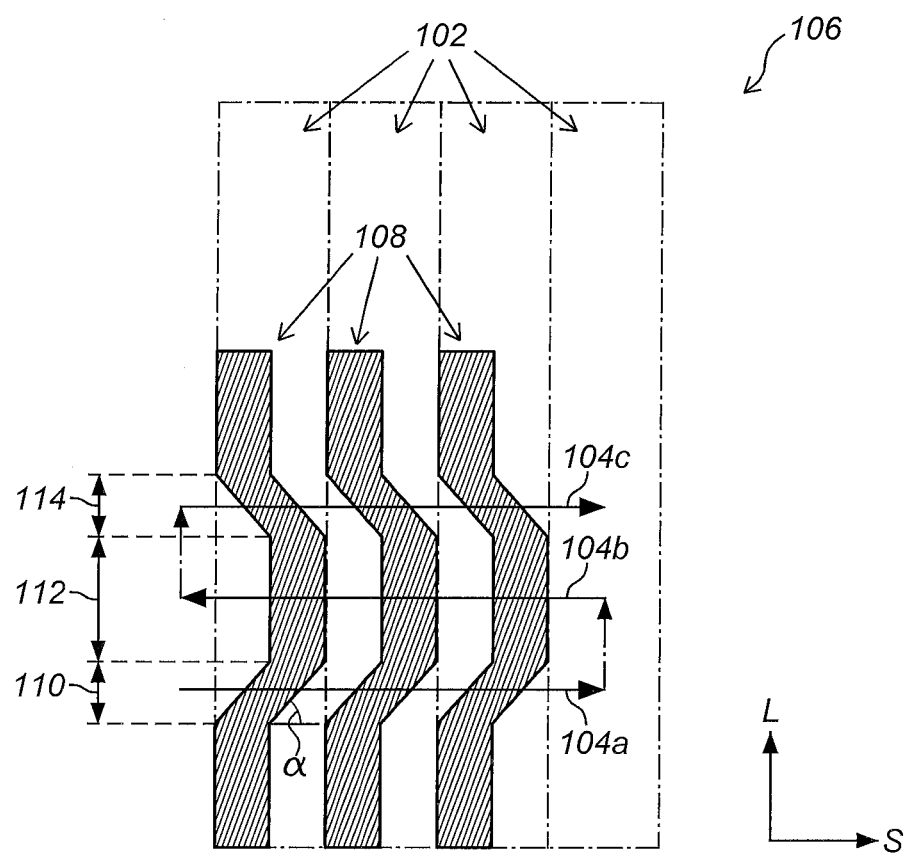
FIG. 7 schematically illustrates an embodiment of a mark for beam position verification.

According to the present disclosure, the lithography system control unit 42 may control the lithography system 1 to write a mark, for example a mark illustrated in FIG. 7, on the target surface, perform optical measurements of the mark and determine compliance of the mark with mark specification data, and based thereon determine whether or not the beams 8 interact with the target surface 10 at the intended positions, i.e., verify individual beam pattern placement accuracy. If pattern placement is found not to comply with specifications, the control unit 42 may control compensation of incorrectly positioned beams and/or recalibration of the system.

FIG. 2A schematically illustrates a beam property sensor 50 for measuring charge particle beam properties, described in U.S. Pat. No. 7,868,300 B2. The sensor 50 comprises a converter element 52 provided with electron blocking elements 54, and a light sensing element 56. Electrons impinging on the converter element 52 are converted into light, which is measured by the light sensing means 56. As illustrated in FIG. 2B measurement data from the light sensing element 56 may be provided to a computational unit Cu which calculates correction data Cor. The correction data Cor is transferred to correction means CM in order to control adjustment of the lithography system, e.g. of one or more beams 8.

Figure 3:
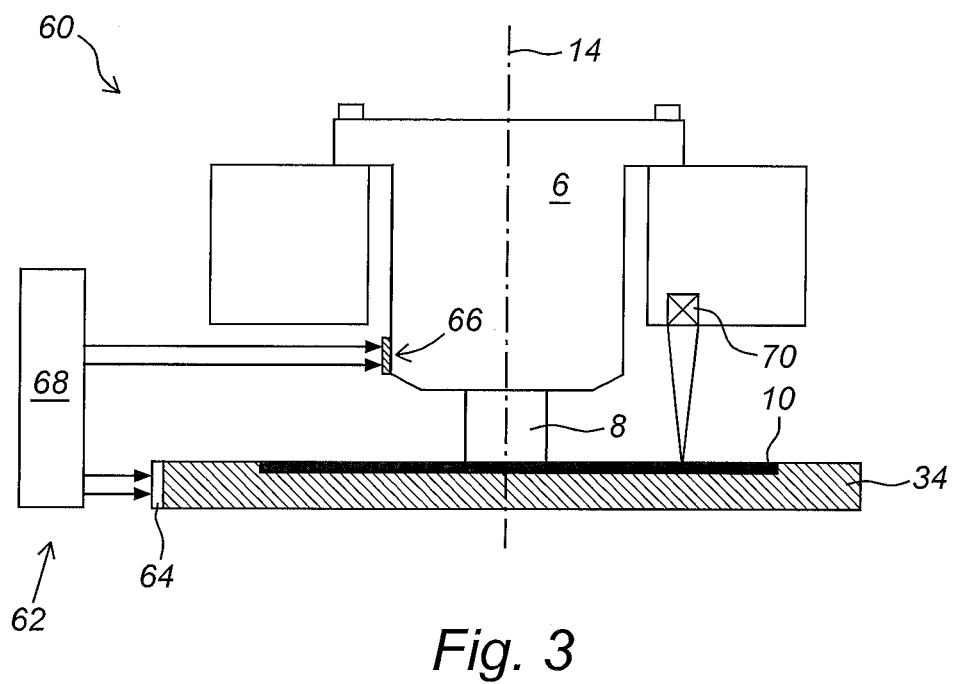
FIG. 3 schematically shows a target alignment sensor arrangement in a multiple beam lithography apparatus.

FIG. 3 schematically shows an alignment sensor arrangement 60 which may be arranged in a multiple beam lithography apparatus 1. Such arrangement is known from US 2012/0268724 A1.

An interferometer sensor arrangement 62 for measuring a position and/or a movement of target support 34 with respect to the electron optical column comprises a chuck position mirror 64 provided on a side surface of the chuck 34, a final projection system position mirror 66 provided on a final portion of the electron optics system 6, and a differential interferometer 68. Preferably, two chuck position mirrors 64 and two final projection system position mirrors 66 are provided, on respectively perpendicularly oriented surfaces on the chuck and the projection system, respectively.

Figure 4:
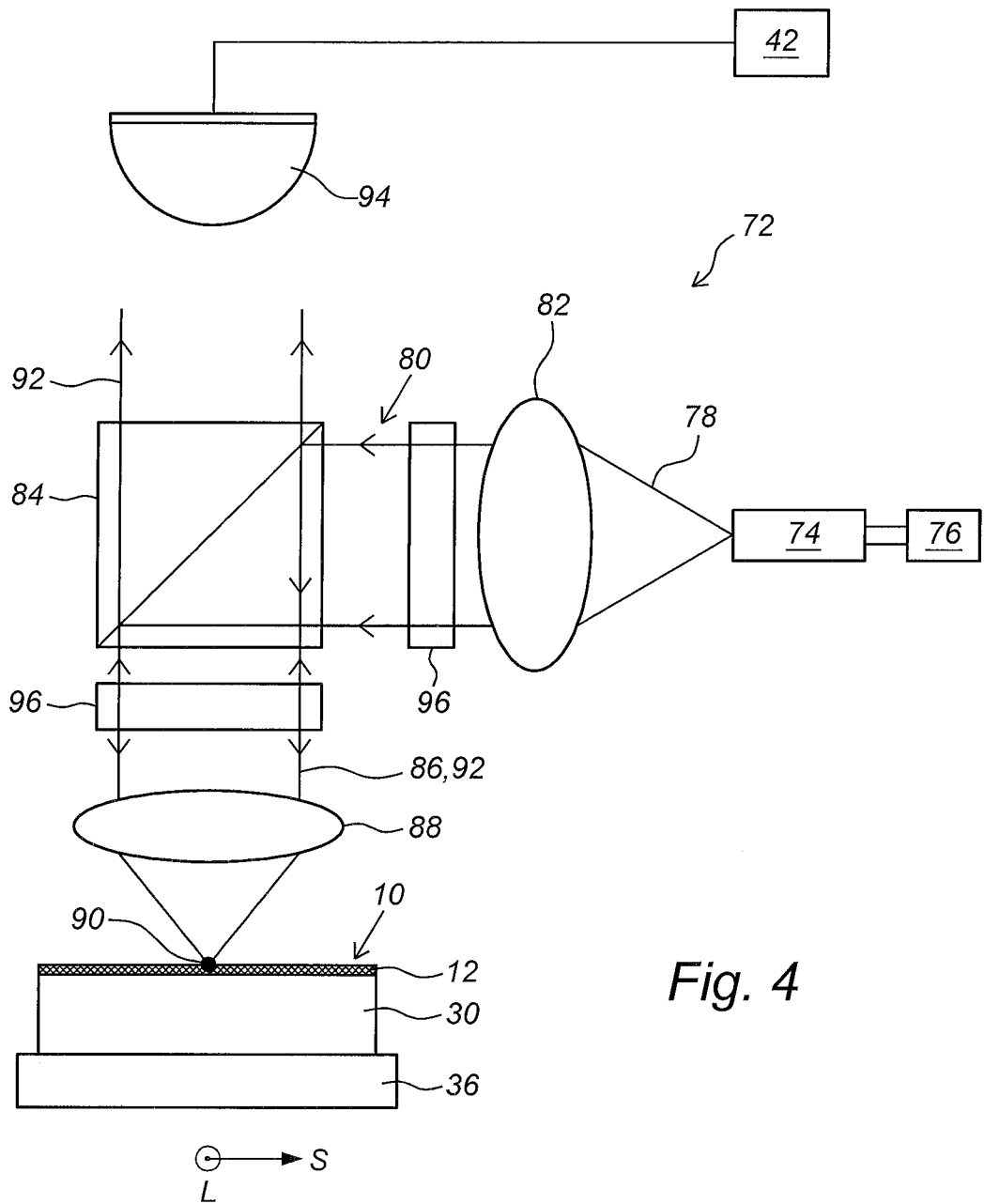
FIG. 4 schematically shows an optical system for mark measurement.

One or more alignment sensors 70 is provided for measuring and verifying positions of chuck position marks and target position marks in order to provide accurate alignment of the target 12 with respect to the electron optical axis 14. The alignment sensor may comprise an optical system as illustrated in FIG. 4. The position of the target 12 may be adjusted by the target support actuators 36, and the position of the chuck 34 relative to the electron optics 6 may be verified using the differential interferometer 68. The lithography control unit 42 may be configured for controlling measurements and receiving and analyzing measurement data obtained with the alignment measurement arrangement 60, and for controlling the actuators 36 such as to align the target 12 with the electron optics 6. Alternatively, a measurement control and/or processing unit, may be provided for this purpose, in communication with the lithography control unit 42.

According to the present disclosure, the alignment sensor 70 may be used for measuring a mark written on the target surface 10 by the lithography system 1 for verification of individual beam pattern placement accuracy within the lithography apparatus 1.

FIG. 4 illustrates an optical system 72 of the alignment sensor 70, which may be used for mark measurements according to the present disclosure. As illustrated in FIG. 3 the optical system 72 may be arranged within the lithography chamber 2. The target support actuator 36 may be configured for moving the target 12 with respect to the optical system 72 in order to perform optical measurements of the mark, preferably performing a plurality of parallel scan lines. For example, the short stroke actuator 20 may provide movement of the target along the first axis S in order to scan the optical beam 86 over the mark written on the target surface 10 by a plurality of electron beams 8 in a multi-beam apparatus 1. The target 12 may be moved along a second axis L, perpendicular to the first axis S, using the long stroke actuator 22.

Figure 9A:
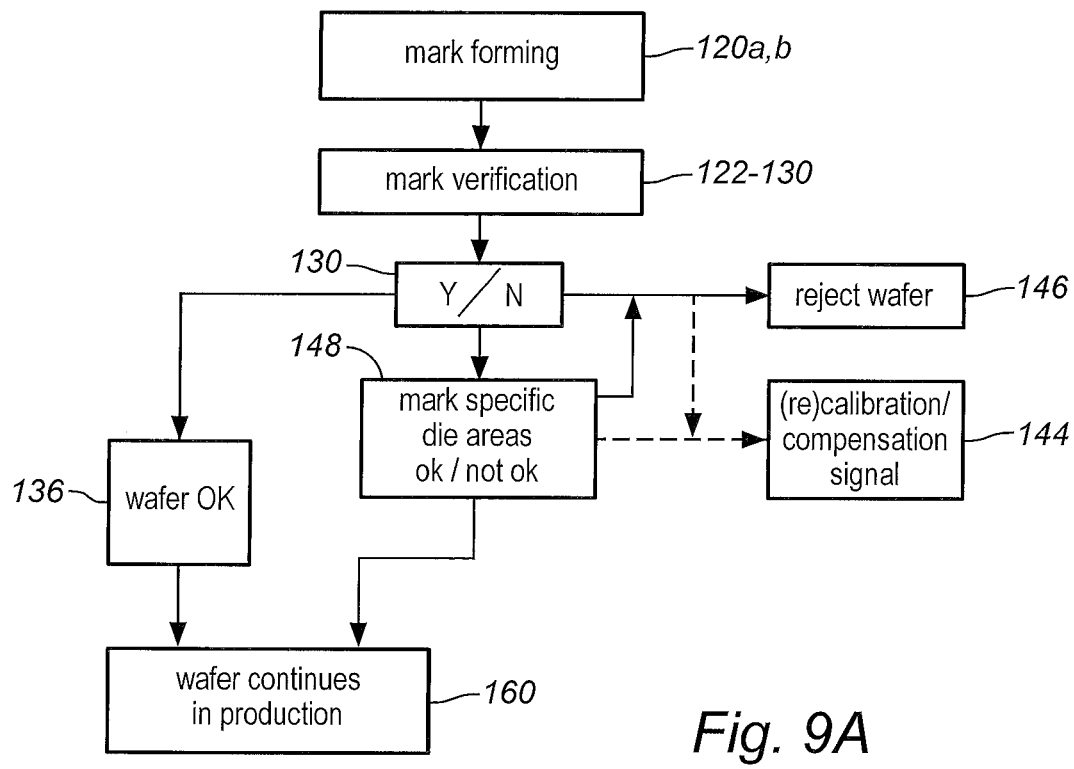
FIGS. 9A and 9B schematically illustrate wafer sorting.
Figure 9B:
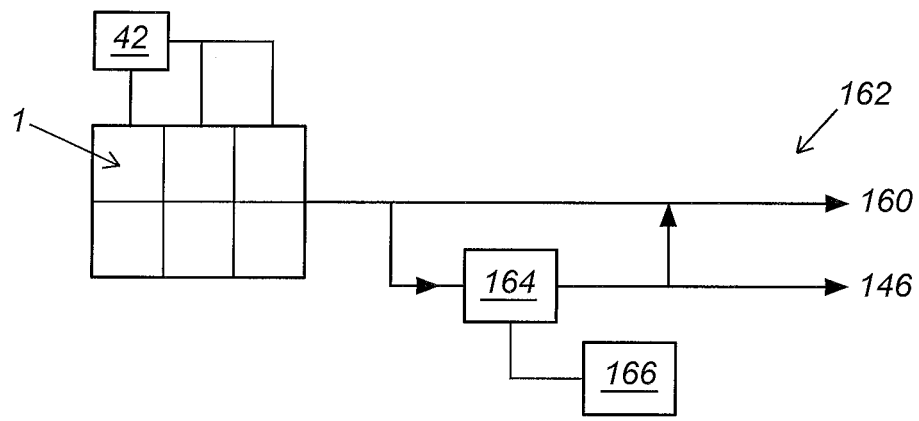

Alternatively, the optical system 72, a target support and an actuator for relatively moving the target support and the optical system may be arranged in a separate measurement chamber, for example as illustrated schematically in FIG. 9B. The actuator may be provided for moving the target while the optical system is kept at a fixed position, or, alternatively, for moving the optical system 72. The optical system 72, the target support 30, and the actuator may form a mark measurement unit. A dedicated control unit may be provided for controlling the measurement and performing calculations for mark verification and/or pattern placement verification.

The optical system 72 illustrated in FIG. 4 comprises an optical fiber 74 for guiding light from a light source 76, such as a laser, which may be located outside the vacuum chamber 2. The light 78 exiting the optical fiber may be collimated into a light beam 80 by a collimator 82. A beam splitter 84 deviates at least a portion of the light 80 to form an optical beam 86, which is focused to a spot 90 on the surface by an optical lens 88. The optical lens 88 further directs the reflected optical beam 92 to the beam splitter 84, which directs at least a part of the reflected optical beam 92 to an optical sensing element 94, such as a photodiode. The optical sensing element 94 is connected to an analysis unit, for example comprised in the control unit 42. The optical beam 86, 92 may be directed perpendicular to the surface 10.

The light source 76 may provide polarized light, in which case the beam splitter 84 may be a polarizing beam splitter and two quarter wave plates 94, 96 may be provided, as described in detail in US 2012/0268724 A1. Alternatively, other variations or embodiments of an optical system may be used for mark measurement and pattern placement verification.

The measurement control unit 42, which may be comprised in the lithography control unit 42 or be in communication therewith, is configured to receive the measured intensity signal from the optical sensing element 92 and to receive a position signal representing a position of the target with respect to the optical beam 86, for example from an interferometer sensor arrangement 62 illustrated in FIG. 3, and to register the intensity signal as a function of the position signal. Alternatively, the position signal may be obtained from actuator control data. From the intensity signal as a function of position on the target surface a measured representation of the mark may be obtained. The measured representation comprises the intensity as a function of the position, and/or parameters calculated from the intensity values as a function of position. The control unit is further configured to compare the measured representation with reference mark data representing an intended definition of the mark, and to determine any deviations between the measured representation and the reference data. The control unit may be further configured to perform verification of individual beam pattern placement accuracy based on the mark verification. Incorrectly positioned beams can be identified by correlating the error position data with one or more beams 8 in the multiple beam lithography apparatus 1. The lithography control unit 42 may be configured to perform compensation or calibration of incorrectly positioned beams based on error position data. Alternatively or additionally, a signal may be provided to a user, indicating that one or more incorrectly positioned beams have been identified.

Figure 5:
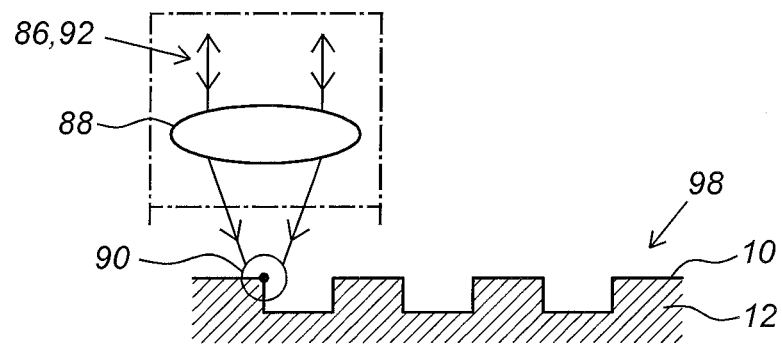
FIG. 5 schematically illustrates the principle of mark measurement.

FIG. 5 schematically illustrates the principle of mark measurement according to the present disclosure. As illustrated in FIG. 5 an optical beam 86 is directed onto the target surface 10, preferably focused to a spot 90, and scanned over a mark or pattern 98 written on the surface 10. The optical system may be arranged such that the optical beam 86 is substantially perpendicular to the plane defined by the target surface 10, whereby the direct reflection 92 is measured. As the beam 86 is scanned over the mark 98 the intensity of the reflected beam 92 is measured, in particular as a function of position along the scan line, for example as function of the relative movement of the beam 86 and the target 12. The intensity of the reflected beam 92 will vary depending on topography and reflectivity of the pattern 98. In FIG. 5, for illustration, the pattern 98 is illustrated as height differences of the target surface 10. However, it is understood that the pattern 98 may equally well be represented by differences in reflectivity of the target surface. Differences in reflection coefficient may arise by processing of the target surface, as conventional in semiconductor fabrication, such as one or more of the steps of resist development, (partial) resist removal, etching of the target surface portions exposed after partial resist removal, deposition of one or more layers on such exposed surface portions, etc.

Figure 6:
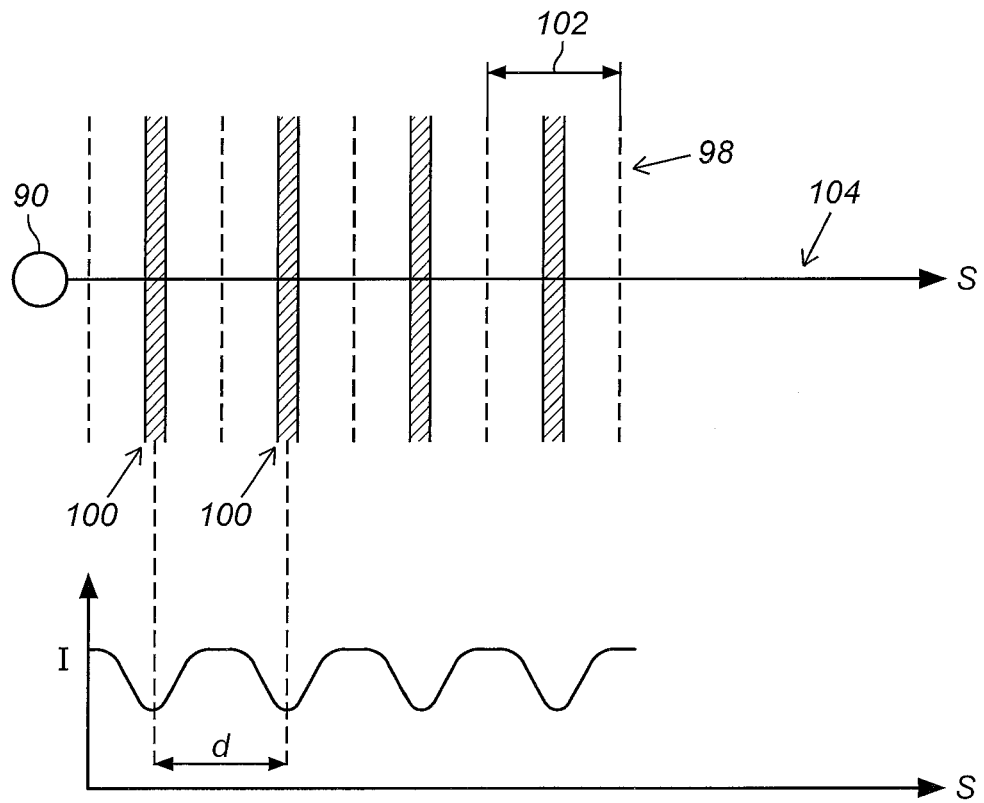
FIG. 6 schematically illustrates the principle of relating the measured signal to features of the mark.

FIG. 6 illustrates an example of a portion of a mark 98, comprising a plurality of parallel lines 100, each formed, or written, by one individual beam 8 during multiple beam lithography, and spaced with a distance d. These lines may correspond to areas having a different optical reflection coefficient and/or different height with respect to the surrounding areas. Each line 100 is positioned centrally within a stripe 102, i.e., within a writing area available for one beam 8. The optical beam 86, in particular the spot 90, may be scanned along one or more scan lines 104 across the mark 98. The lower part of FIG. 6 illustrates an intensity curve measured as the spot 90 is scanned over the mark 98 along the scan line 104. The periodicity of a test mark for beam position verification and the size of the beam spot 90 may have a relation such that the diameter of the beam spot 90 equals half the periodicity of the test mark. The features of the mark may have a dimension along the first axis S substantially corresponding to the diameter of the beam spot 90. In the illustrated example, the pattern written by the respective electron beams 8, e.g. the lines 100, form areas of lower reflectivity, giving rise to minima in the intensity curve. By calculating the distance d between adjacent minima a measured representation is obtained. By comparing each of the distances d obtained from the intensity measurement data with the intended distances defined by mark specification data conclusions regarding pattern placement can be made. If each of the distances d complies with the specification data, that is, if no distance d deviates more than a predetermined limit, all beams 8 may be deemed to be correctly positioned on the target surface 10. However, if one or more of the distances d do not comply with the specifications, that is, the measured distances deviates from the specification by more than the predetermined limit, pattern placement is not correct. Beams having written erroneously positioned pattern features is not correctly positioned. Incorrectly positioned beams can thus be identified. Error position data can be determined, specifying positions where the measured representation deviates from the reference mark data by more than the predetermined limit.

Thereby, it can be identified which electron beams are incorrectly positioned on the target surface. For example, if each electron beam writes one line 100, whereby the number of lines in the mark 98, or a mark section, equals the number of electron beams 8 used in the multi beam lithography process, an error in position of line number n indicates that beam number n is not correctly positioned on the surface 10.

FIG. 7 schematically illustrates a mark 106 which may be used for beam position verification. Such test mark allows for verification of beam positions in two dimensions. In particular, contributions from each beam in along the first axis and along the second axis on the target surface can be deducted from measurements of such mark. An example of such test mark is illustrated in FIG. 7. However, it should be understood that also other forms of test marks may be used. The mark 106 comprises a number of lines 108 each formed by one individual beam 8 during the multiple beam lithography process. Each stripe 102 comprises one line 108. The number of lines 108 in the mark 106 preferably corresponds to at least the number of beams 8 used in the lithography apparatus 1. The mark 106 can be divided into portions in which the lines 108 form straight, parallel line portions. The mark 106 illustrated in FIG. 7 comprises a first portion 110 wherein the lines 108 form straight line portions oriented at an oblique angle α with respect to the first axis S, a second portion 112 wherein the parallel lines form straight line portions oriented perpendicular to the first axis S, and a third portion 114 wherein the parallel lines 108 form straight line portions oriented at an oblique angle α+90° with respect to the first axis S. The angle α preferably has a value of 45°. In general, the first axis correspond to the short stroke axis S, and the second axis to the long stroke axis L, also referred to as the mechanical scan direction, the stripes 102 being aligned along the long stroke axis L. Each portion 110, 112, 114 preferably has an extension along the second axis L of the same order of magnitude as the width of a stripe 102. In particular, the stripe width may be 2 μm.

For beam position verification, the lithography system control unit 42 controls the lithography system to write a mark according to specifications, for example a mark 106 illustrated in FIG. 7. The written mark is subsequently measured by a mark measurement unit, such as the alignment sensor 70 comprising an optical system 72 illustrated in FIGS. 3 and 4, in order to obtain a measured representation of the written mark 106. As illustrated in FIG. 7, a first scan line 104a is performed across the first portion 110, a second scan line 104b across the second portion 112, and a third scan line 104c across the third portion 114. The spacing between the scan lines may be on the same order of magnitude as the stripe width. The mark measurement may be performed within the lithography chamber 2, after having performed one or more semiconductor processing steps of the target surface outside the vacuum chamber. Although properties of the resist layer are changed upon impact of beams during the lithography process, these changes are usually not visible in optical reflection measurements. Therefore, at least the step of resist development is performed prior to mark measurement. Commonly, development of the resist will give rise to an optically visible pattern on the target surface. Further processing steps, such as etching and/or deposition of material may provide for topographic and/or reflection coefficient variations visible in reflection intensity measurements. Such semiconductor processing steps are known in the field. Mark measurement, and beam position verification based on the mark measurement, may thus be performed either as a separate verification step, or prior to a subsequent lithographic exposure session. The control unit 42 may control the target actuator 36, e.g. the short stroke actuator 38 and the long stroke actuator 40, to perform scan lines 104 as described above.

A measured representation of the written mark 106 may be obtained by calculating distances between all adjacent lines 108 covered by the scan lines 104a,104b,104c from the measurement data. Beam positions along the first axis S may be verified from the second scan line 104b performed across the second portion 112, and beam positions along the first and second axis can be verified by combining results from the second scan line 104b and the first and/or third scan lines 104a, 104c. By scanning the optical beam 86 across lines 108 comprised in the mark 106, the scan line having at least an extent covering a portion of the mark comprising contributions from each beam 8, and over all portions 110, 112, 114, two dimensional pattern placement data can be determined for each beam 8 used for forming the mark 106. Based on the measured representation of the test mark, and eventual corresponding error position data, incorrectly positioned beams can be identified.

This test mark 106, having all features formed in one layer, enables pattern placement verification. In multiple beam lithography, accurate pattern placement gives an indication of correct stitching properties, i.e., highly accurate pattern formation in boundary regions of adjacent stripes. Overlay can be verified by forming a first set of features in one layer, and subsequently, in a second lithography process, a second set of test mark features in a second layer, on top of the first set of features. By measuring the position of features within one layer with respect to features in one or more other layers, conclusions regarding accuracy of overlay can be made.

According to the present disclosure, individual beam pattern placement measurements may be performed within the lithography chamber, in a short amount of time, thereby allowing for substantially direct adjustment of the system. The beam position verification described herein may be performed as a complement to the beam measurements known from the prior art. Thereby, different measurements of various beam properties may be performed. Further, the functioning of the respective sensors may be verified.

Figure 8:
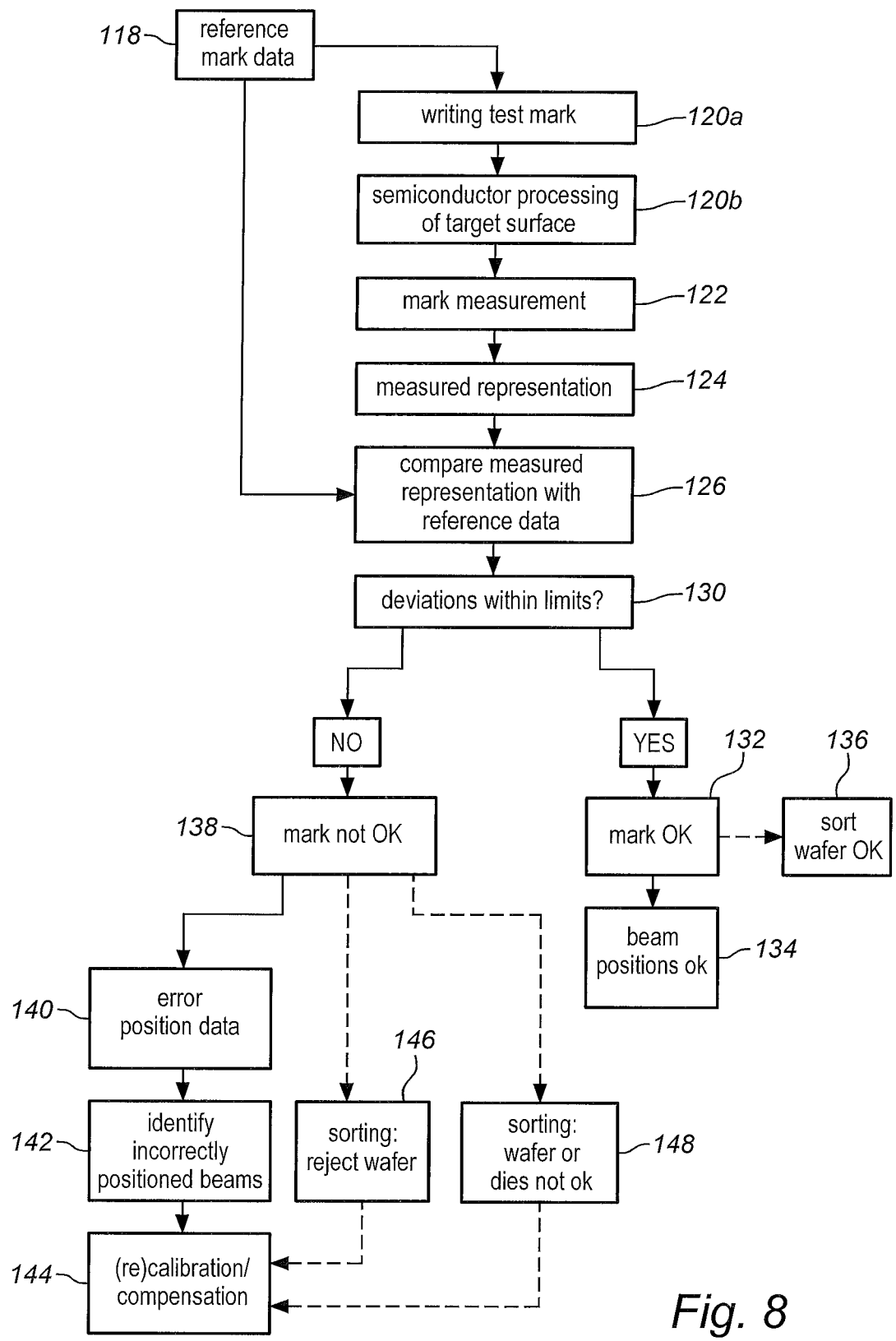
FIG. 8 shows a flow chart of mark verification, beam position verification and/or wafer sorting.

FIG. 8 shows a flow chart illustrating mark verification, beam position verification, and wafer sorting. Verification of a mark 98 written on a target surface 10 during multi beam lithography may not only be used for beam position verification, but may also provide an estimate of the correctness of patterns formed on the target surface 10, for example for wafer sorting at different stages in a wafer fabrication process.

In a first step 120 a mark 98, 106, defined by reference mark data 118, is written in the resist layer of the target surface 10 using the lithography system 1. Subsequently, the target is removed from the lithography chamber, and subjected to semiconductor processing in order to reveal an optically measurable pattern, as described above, indicated by step 121.

After processing the target surface, the target is positioned back into the lithography chamber or in a separate measurement chamber, and mark measurements 122 are performed on the mark 98, 106, for example using the optical system 72 illustrated in FIG. 4. For pattern placement verification the measurement may be performed within the lithography chamber 2. For wafer sorting the mark measurement 122 may be performed in a separate measurement chamber. In step 124 a measured representation is calculated from the measured intensity of the reflected light 92 as a function of target position data, which may be obtained from e.g.

position measurement data or from actuator control data. As described with reference to FIG. 3, the position of the target 12 with respect to the optical axis 14 of the lithography system can be determined using a differential interferometer 86. The measured representation may comprise one or more parameters calculated from the measurement data, for example distance values between features in the mark 98, 106. In step 126, the measured representation is compared with reference mark specification 118, which may be stored in a memory of a control unit controlling mark verification. In step 130 any deviations between the measured representation and the specification are determined and compared with a predetermined limit. If all deviations are within the predetermined limit the mark is verified, step 132. In the beam position verification method, this is indicates that all beams 8 are correctly positioned on the target surface 10, and beam positions are verified in step 134. This may provide an indication that the lithography apparatus is functioning according to specifications. If mark verification is used for wafer sorting purposes, the wafer may be deemed OK, and sorted for further processing 136.

If at least one deviation is not within the predetermined limit, the mark correctness is not verified, step 138. It may be deducted that not all beams 8 are correctly positioned. In step 140, error position data is calculated, specifying where the measured representation, and thus the mark 98, 106 written on the target surface 10, deviates from the reference data 118 by more than the predetermined limit. The error position data thus identifies which features of the mark are not correctly written. From this data in step 142, incorrectly positioned beams 8 can be identified. In step 144 incorrectly positioned beams can be compensated, as described above, or recalibration of the lithography apparatus may be performed. The wafer, or parts thereof, comprising an incorrectly written mark may be rejected, or marked as not complying with specifications, steps 148, 150.

FIG. 9A illustrates a flow chart for wafer sorting performed using the mark verification method described herein. The wafer is patterned, including forming one or marks 98, 106 thereon in step 120, subjected to processing steps 121 of the target surface, and subsequently the mark is verified, according to steps 122-130. As illustrated in FIG. 9B mark measurement and verification may take place in a separate measurement chamber 164 located downstream a multi beam lithography system 162. If the mark complies with specification data, the wafer may be considered OK 136, and sorted to continue in the production line, step 160. If the mark does not comply with specifications, the wafer may be rejected, 146. Marks provided on the wafer may be related to specific wafer areas, in particular specific die areas. After verification of these test marks the corresponding areas may be marked as OK or not OK, 176. For example, the die areas may be marked by a dye, or otherwise indicated. The wafer may in this case either be allowed to continue for further processing, 160, or rejected, 146.

A system adjustment signal may be issued 144, for example transmitted to a lithography control unit 42 to initiate compensation, or calibration, of the lithography apparatus 1. Alternatively or additionally, a signal indicating the presence of incorrect marks may be provided to a user. In particular, such signals may be issued when the mark repeatedly does not comply with specifications. Occasional occurrence of erroneous marks may be considered to have other causes than incorrectly positioned beams 8 in the lithography apparatus 1.

Wafer sorting may be performed by a wafer sorting apparatus 162 illustrated in FIG. 9B, comprising a separate measurement chamber 164 and control unit 166. As illustrated in FIG. 9B, a lithography system may comprise a plurality of lithography apparatuses 1 and one or more lithography control unit 42. All wafers, or e.g. randomly selected wafers, outputted from the lithography system may be subjected to mark verification measurements. Mark verification may provide an indication that the pattern formed on the wafer surface is likely to comply with specifications.

Figure 10:
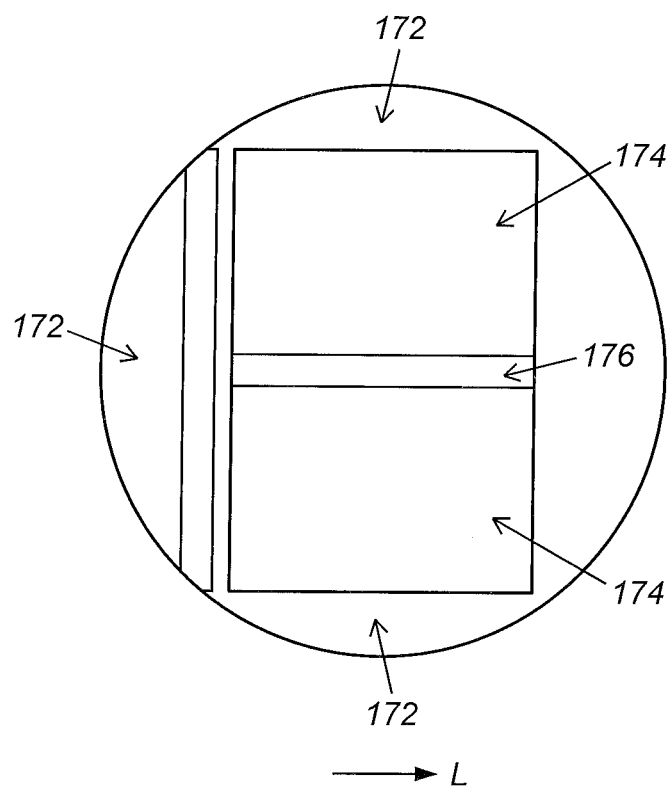
FIG. 10 schematically shows examples of locations of test marks on a wafer surface.

As illustrated schematically in FIG. 10, a target surface 10 may be provided with marks in a plurality of different regions. For example one or more substantially peripheral regions 172 may be provided with marks. Regions 174 illustrate regions comprising fields intended for patterning, e.g. forming integrated circuits. For example, marks may be written on peripheral portions of the target surface. Alternatively or additionally, marks may be provided in areas 176 associated with die areas or groups of die areas.

The disclosure has been described by reference to certain embodiments discussed above. These embodiments are susceptible to various modifications and alternative forms without departing from the scope of protection defined in the accompanying claims.

The invention claimed is:

1. A method for verification of a mark written on a target surface in a multiple beam lithography process, the method comprising:
  mark measurement, comprising:
    directing, and preferably focusing, an optical beam onto said target surface;
    measuring a reflected optical beam generated by reflection of said optical beam by said surface;
    moving said optical beam and said target with respect to one another such that said optical beam is scanned over at least one scan line across at least a portion of said mark in a direction parallel to a first axis;
    measuring an intensity of said reflected optical beam as a function of position along said scan line; and
  obtaining a measured representation of said mark, said measured representation comprising intensity as a function of position along said scan line and/or parameters calculated from said intensity;
  comparing said measured representation with reference mark data representing an intended definition of said mark and determining any deviation between said measured representation and said reference mark data.

2. Method according to claim 1, comprising:
  if said deviation is not within a predetermined limit, determining error position data specifying positions where said measured representation deviates from said reference mark data by more than said predetermined limit.

3. Method according to claim 1, wherein said optical beam is scanned over a plurality of parallel scan lines, wherein preferably a spacing between said parallel scan lines is of the same order of magnitude as a stripe width.

4. Method according to claim 1, wherein said measured representation is obtained by calculating distances between adjacent features comprised within said mark, calculating said distances between all of said features within said scan lines, and calculating said distances for each scan line.

5. Method according to claim 2, comprising:
  writing a mark on said target surface using a multiple beam lithography apparatus,
  determining individual beam pattern placement accuracy based on verification of said mark, comprising determining that one or more of the beams are incorrectly positioned if one or more of said deviations is not within said predetermined limit, the method preferably comprising identifying said incorrectly positioned beams using said error position data.

6. Method according to claim 5, wherein said mark measurement is performed within said multiple beam lithography apparatus.

7. Method according to claim 5, wherein said mark enables verification of individual beam positions in two dimensions on the target surface for each beam used for writing said mark, said mark preferably comprising at least one feature written by each individual beam; enabling verification of a beam position along the first axis, said at least one feature further enabling, or at least one additional feature written by each individual beam, enabling verification of a beam position along a second axis substantially perpendicular to said first axis, wherein preferably said scan line extends over at least a plurality, preferably all, of said at least one feature comprised in said mark.

8. Method according to claim 7, said mark comprising a number of lines each written by one beam during said multiple beam lithography, said number of lines at least corresponding to a number of beams used during said lithography, said mark comprising:

a first portion wherein said lines form straight parallel line portions oriented at an oblique angle α with respect to said first axis, a second portion wherein said lines form straight parallel line portions oriented perpendicular to said first axis, and a third portion wherein said lines form straight parallel line portions oriented at an oblique angle α+90° with respect to said first axis, wherein said angle α preferably has a value of substantially 45°.

9. Method according to claim 8, wherein a first scan line is performed within said first portion, a second scan line within said second portion, and a third scan line within said third portion, and a position of a beam along said first axis is determined from said intensity measured along said second scan line, and by combining said intensity measured along said second scan line and said first and/or third scan line a position of said beam along said first axis and said second axis are determined, and wherein said positions are determined for each beam used for writing said test mark.

10. Method according to claim 5, wherein features within said mark are related to individual beams by determining a position of said target with respect to a lithography apparatus reference point.

11. Method according to claim 5, comprising verifying overlay, whereby said mark comprises a first set of features written in a first layer and a second set of features written in a second layer, said second set formed on top of said first set.

12. Method according to claim 5, comprising performing calibration and/or compensation of incorrectly positioned beams based on said individual beam position verification.

13. Method according to claim 1, further comprising sorting wafers provided with one or more marks based on verification of said mark.

14. Method according to claim 13, wherein said wafer is provided with a plurality of said marks each associated with one or more areas, comprising sorting said areas based on whether or not said marks comply with said reference mark data.

15. A system for verification of a mark written on a target surface by a multiple beam lithography process, the system comprising:

a mark measurement unit, comprising:

an optical system for directing, and preferably focusing, an optical beam onto said target surface and receiving a reflected optical beam generated by a reflection of said optical beam by said surface, and for generating an intensity signal representing an intensity of said reflected optical beam;

a target support for supporting said target; and an actuator for moving said optical system and said target support with respect to one another along at least a first axis, such that said optical beam may be scanned along at least one scan line over at least a portion of said mark;

a control unit configured to:

receive said intensity signal, receive a position signal representing a position of said target with respect to said optical system, register said intensity signal as a function of said position signal, obtain a measured representation of said mark, said measured representation comprising said intensity as a function of position and/or parameters calculated from said intensity values, compare said measured representation with reference mark data representing an intended definition of said mark and determining any deviation between said measured representation and said reference mark data.

16. System according to claim 15, said control unit configured to determine error position data specifying positions where said measured representation deviates from said reference mark data by more than a predetermined limit.

17. System according to claim 15, wherein said actuator is configured to move said target support and said optical beam with respect to one another along a second axis substantially perpendicular to said first axis, wherein said actuator may control position along said second axis with an accuracy at least corresponding to a stripe width.

18. System according to claim 15, wherein said control unit is configured to obtain said measured representation by calculating distances between adjacent features comprised within said mark.

19. System according to claim 15, wherein said control unit is further configured to verify beam positions on said target surface during a multiple beam lithography process based on verification of a mark written during said process, said control unit preferably configured to identify incorrectly positioned beams based on said error position data.

20. System according to claim 16, wherein said control unit is further configured to sort wafers or parts of said wafer provided with one or more marks based on verification of said mark.

21. A multiple beam lithography apparatus comprising:

a lithography chamber comprising a target support and a target support actuator adapted to move said target support along at least said first axis, a system according to claim 20 for verification of individual beam positions on said target surface, said mark measurement unit arranged within said lithography chamber, and said actuator unit being said target support actuator, a lithography control unit configured to control said multiple beam lithography apparatus, and comprising or being configured to communicate with said control unit, said lithography control unit preferably configured to control said lithography apparatus to write a mark on said surface and to verify beam positions on said surface based on verification of said mark.

22. Apparatus according to claim 21 comprising a target alignment sensor arrangement to determine and control a relative position of said target support and a lithography apparatus reference point and for determining a relative position of said target and said target support, wherein preferably said alignment sensor arrangement comprises said optical system, preferably also said actuator and/or said control unit.

23. Apparatus according to claim 21, wherein said lithography control unit is configured to perform calibration and/or compensation of incorrectly positioned beams.

24. A non-transitory computer readable medium comprising a computer program for verifying position of beams on a target in a multiple beam lithography apparatus, especially an apparatus according to claim 21, said computer program comprising instructions to cause one or more processors to:

control said lithography apparatus to write a mark on a target surface;

control an actuator to move an optical beam and said target relative one another, such that said optical beam is scanned over at least a portion of said mark;

record an intensity of a reflected optical beam as a function of position of said optical beam with respect to said target;

determine a measured representation of said mark, said measured representation comprising intensity as a function of position and/or parameters calculated from said intensity;

compare said measured representation with reference mark data representing an intended definition of said mark;

determine any deviation between said measured representation and said reference mark data;

if said deviation is not within said predetermined limit, determine error position data specifying positions where said measured representation deviates from said reference mark data by more than said predetermined limit;

identify incorrectly positioned beams based on said error position data.

25. The non-transitory computer readable medium according to claim 24, wherein the instructions further cause the one or more processors to control compensation of incorrectly positioned beams.

* * * * *